United States Patent [19]

Kinsho et al.

[11] Patent Number: 5,527,490
[45] Date of Patent: Jun. 18, 1996

[54] SILACYCLOHEXANE CARBALDEHYDE COMPOUNDS AND PROCESSES FOR PREPARING SILACYCLOHEXANE-BASED LIQUID CRYSTAL COMPOUNDS FROM THE CARBALDEHYDE COMPOUND

[75] Inventors: Takeshi Kinsho; Takaaki Shimizu; Tsutomu Ogihara; Tatsushi Kaneko; Mutsuo Nakashima, all of Niigata-ken, Japan

[73] Assignee: Shin-Etsu Chemical Co., Ltd., Tokyo, Japan

[21] Appl. No.: 434,814

[22] Filed: May 4, 1995

[30] Foreign Application Priority Data

May 11, 1994 [JP] Japan .................................... 6-123208

[51] Int. Cl.$^6$ .............................. C09K 19/30; G02F 1/13; C07F 7/08
[52] U.S. Cl. ................... 252/299.61; 252/299.66; 359/103; 556/406
[58] Field of Search ................... 252/299.61, 299.66; 556/406; 359/103

[56] References Cited

U.S. PATENT DOCUMENTS

| | | | |
|---|---|---|---|
| 4,973,723 | 11/1990 | Cawthon et al. | 556/406 |
| 5,454,977 | 10/1995 | Shimizu et al. | 252/299.61 |

FOREIGN PATENT DOCUMENTS

| | | |
|---|---|---|
| 630903 | 12/1994 | European Pat. Off. . |
| 632044 | 1/1995 | European Pat. Off. . |
| 648773 | 4/1995 | European Pat. Off. . |
| 650969 | 5/1995 | European Pat. Off. . |
| 657460 | 6/1995 | European Pat. Off. . |

OTHER PUBLICATIONS

Washburn, S. S. et al., "Acetolysis of 4,4-disubstituted 4-silacyclohexyl tosylates: Effect of remote silicon substitution on organic reactivity." *Journal of Organometallic Chemistry*, vol. 133, 1977, pp. 7–17.

*Primary Examiner*—Shean C. Wu
*Attorney, Agent, or Firm*—Lowe, Price, LeBlanc & Becker

[57] ABSTRACT

A silacyclohexane carbaldehyde compound of the following formula (I)

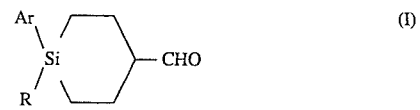

wherein Ar represents a phenyl group or a tolyl group, and R represents a phenyl group, a tolyl group, a linear alkyl group, a mono or difluoroalkyl group, a branched alkyl group, an alkoxyalkyl group or an alkenyl group. Processes for preparing a silacyclohexane-based liquid crystal compound of the following formula (II) or (III) from the silacyclohexane carbaldehyde are also described

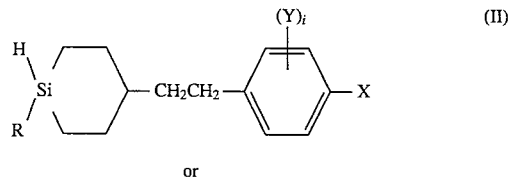

or

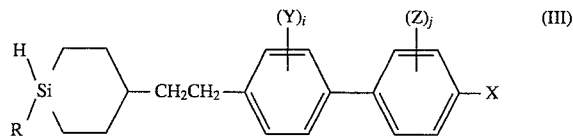

wherein X represents CN, F, Cl, $CF_3$, $CClF_2$, $CHClF$, $OCF_3$, $OCClF_2$, $OCHF_2$, $OCHClF$, $(O)_m CT=CX_1X_2$, $O(CH_2)_r(CF_2)_sX_3$, R or OR wherein m is a value of 0 or 1, T and $X_1$ independently represent H, F or Cl, $X_2$ represents F or Cl, r and s are, respectively, a value of 0, 1 or 2 provided that r+s=2, 3 or 4, $X_3$ represents H, F or Cl, and R has the same meaning as defined before, Y and Z independently represent a halogen or a methyl group, i and j are independently a value of 0, 1 or 2.

14 Claims, No Drawings

SILACYCLOHEXANE CARBALDEHYDE COMPOUNDS AND PROCESSES FOR PREPARING SILACYCLOHEXANE-BASED LIQUID CRYSTAL COMPOUNDS FROM THE CARBALDEHYDE COMPOUND

BACKGROUND OF THE INVENTION

1. Field of the Invention

This invention relates to a silacyclohexane carbaldehyde compound and also to a process for preparing a silacyclohexane-based liquid crystal compound using the carbaldehyde compound.

2. Description of the Prior Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect) and has a twisted nematic structure.

Although the properties of the liquid substances used in these liquid crystal devices depend, more or less, on the type of display, it is commonly required that the liquid crystal substances have a wide range of liquid crystal working temperatures and that they are stable against moisture, air, light, heat, electric field and the like. Moreover, the liquid crystal substances should desirably be low in viscosity and should ensure a short address time, a low threshold voltage and a high contrast in a cell.

As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which could satisfy the needs for on-vehicle materials and an improvement in low temperature performance.

Under these circumstances, we developed novel silacyclohexane-based liquid crystal compounds which contain a silicon atom in the molecule so that the characteristic properties for use as a liquid crystal substance are improved, and proposed in our earlier Japanese Patent Application as will be set out hereinafter.

SUMMARY OF THE INVENTION

It is an object of the invention to provide a silacyclohexane carbaldehyde compound which is an intermediate useful for preparing silacyclohexane-based liquid crystal compounds.

It is another object of the invention to provide a process for preparing a silacyclohexane-based liquid crystal compound which is a kind of derivative of the silacyclohexane carbaldehyde compound.

The above objects can be achieved, according to one embodiment of the invention, by a silacyclohexane carbaldehyde compound of the following formula (I)

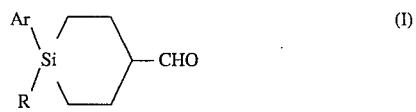

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms.

The silacyclohexane carbaldehyde compound of the above formula (I) is useful as an intermediate for a silacyclohexane-based liquid compound of the following general formula (II)

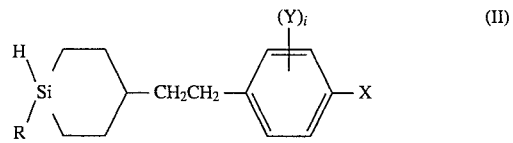

wherein R has the same meaning as defined above and represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, X represents CN, F, Cl, $CF_3$, $CClF_2$, $CHClF$, $OCF_3$, $OCClF_2$, $OCHF_2$, $OCHClF$, $(O)_mCT=CX_1X_2$, $O(CH_2)_r(CF_2)_sX_3$, R or OR wherein m is a value of 0 or 1, T and $X_1$ independently represent H, F or Cl, $X_2$ represents F or Cl, r and s are, respectively, a value of 0, 1 or 2 provided that r+s=2, 3 or 4, $X_3$ represents H, F or Cl, and R has the same meaning as defined above, Y represents a halogen or a methyl group, i is a value of 0, 1 or 2, or a silacyclohexane-based liquid crystal compound of the following general formula (III)

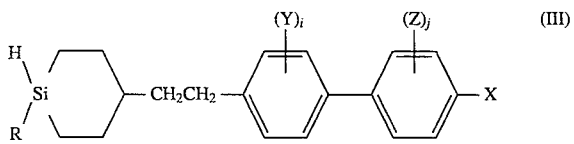

wherein R, Y, X and i have, respectively, the same meanings as defined with respect to the formula (II), Z represents a halogen or a methyl group, and j is zero or an integer of 1 or 2.

The silacyclohexane-based liquid crystal compound of the general formula (II) is prepared according to a process of the invention which comprises:

reacting the silacyclohexane carbaldehyde of the general formula (I) with a ylide compound of the following general formula (IV)

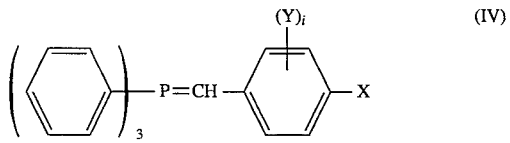

wherein X has the same meaning as defined with respect to the formula (II) and represents CN, F, Cl, $CF_3$, $CClF_2$, $CHClF$, $OCF_3$, $OCClF_2$, $OCHF_2$, $OCHClF$, $(O)_mCT=CX_1X_2$, $O(CH_2)_r(CF_2)_sX_3$, R or OR wherein m is a value of 0 or 1, T and $X_1$ independently represent H, F or Cl, $X_2$ represents F or Cl, r and s are, respectively, a value of 0, 1 or 2 provided that r+s=2, 3 or 4, $X_3$ represents H, F or Cl, and R has the same meaning as defined above, Y represents a halogen or a methyl group, i is a value of 0, 1 or 2, thereby obtaining a compound of the following formula (V)

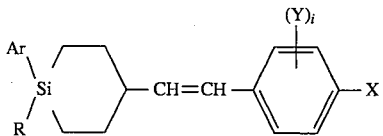 (V)

subjecting the thus obtained compound of the formula (V) to hydrogenation to obtain a compound of the following general formula (VI)

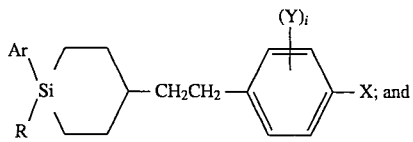 (VI)

further subjecting the compound of the formula (VI) to de-silylation and then to reduction to obtain a compound of the general formula (II)

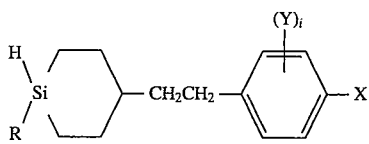 (II)

In the above formulas (V) to (VI), At, R. Y, X and i have, respectively, the same meanings as defined hereinbefore.

Moreover, the silacyclohexane-based liquid crystal compound of the general formula (III) can be prepared by a process which comprises:

reacting a silacyclohexane carbaldehyde compound of the afore-indicated general formula (I) with a ylide compound of the following general formula (VII)

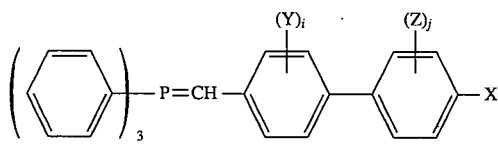 (VII)

wherein X represents CN, F, Cl, $CF_3$, $CClF_2$, $CHClF$, $OCF_3$, $OCClF_2$, $OCHF_2$, $OCHClF$, $(O)_mCT=CX_1X_2$, $O(CH_2)_r(CF_2)_sX_3$, R or OR wherein m is a value of 0 or 1, T and $X_1$ independently represent H, F or Cl, $X_2$ represents F or Cl, r and s are, respectively, a value of 0, 1 or 2 provided that r+s=2, 3 or 4, $X_3$ represents H, F or Cl, and R has the same meaning as defined before, Y and Z independently represent a halogen or a methyl group, i and j are independently a value of 0, 1 or 2, thereby obtaining a compound of the following general formula (VIII)

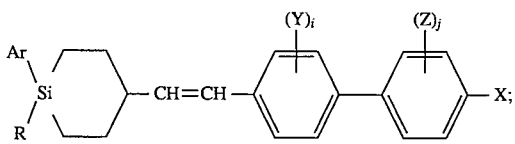 (VIII)

subjecting the compound of the formula (VIII) to hydrogenation to obtain a compound of the following general formula (IX)

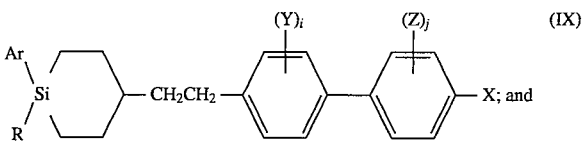 (IX)

further subjecting the thus obtained compound of the formula (IX) to de-silylation and then to reduction to obtain a compound of the general formula (III)

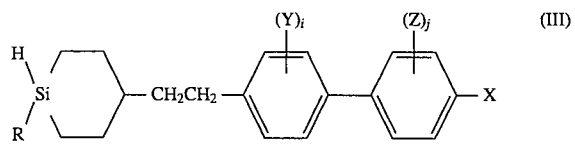 (III)

In the general formulas (VIII) and (IX), Ar, R, X, Y, Z, i and j have, respectively, the same meanings as defined hereinbefore and whenever appearing hereinafter and may not be again defined in some cases.

Alternatively, the silacyclohexane-based liquid crystal compound of the general formula (III) can also be prepared according to a process which comprises:

reacting a silacyclohexane carbaldehyde of the afore-indicated general formula (I) with a ylide compound of the following general formula (X)

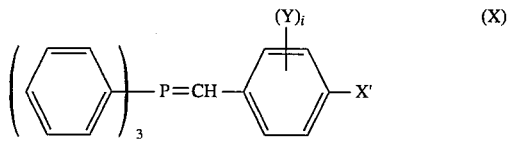 (X)

wherein X' represents a halogen, Y represents a halogen or a methyl group, and i is a value of 0, 1 or 2, thereby obtaining a compound of the following general formula (XI)

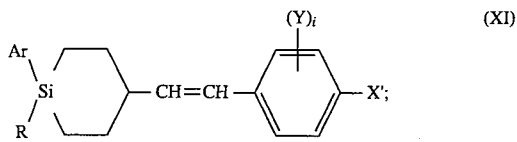 (XI)

subjecting the compound of the formula (XI) to hydrogenation to obtain a compound of the following general formula (XII)

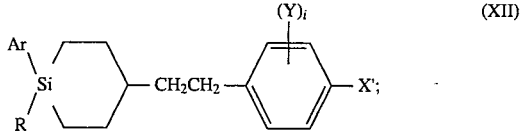 (XII)

further subjecting the compound of the formula (XII) to reaction with an organometal compound of the following general formula (XIII) in the presence of a transition metal catalyst

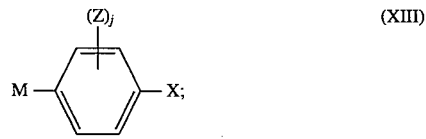 (XIII)

wherein M represents MgU or ZnU wherein U represents a halogen, or $B(OV)_2$ wherein V represents a hydrogen atom or an alkyl group and Z has the same meaning as defined hereinbefore, thereby obtaining a compound of the following general formula (XIV)

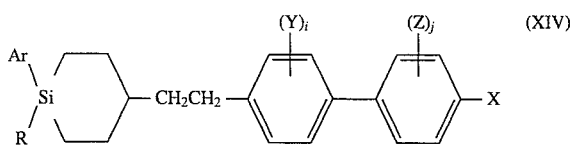

subjecting the compound of the formula (XIV) to desilylation and then to reduction to obtain a silacyclohexane-based liquid crystal compound of the following general formula (III)

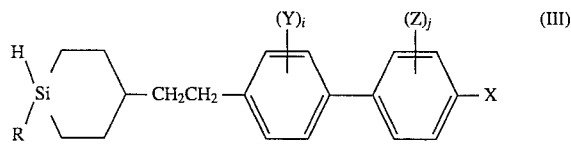

DETAILED DESCRIPTION OF THE INVENTION

The embodiments of the invention are described. It will be noted that Ar, R, X, X', Y, Z, i, and j which have, respectively, been defined in the foregoing formulas have, respectively, the same meanings as defined hereinbefore and may not be again defined in such formulas appearing hereinafter.

According to one embodiment of the invention, there is provided a silacyclohexane carbaldehyde compound of the following general formula (I)

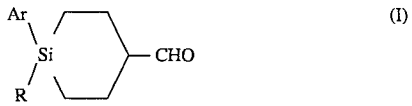

wherein Ar represents a phenyl group or a tolyl group, R represents a phenyl group, a tolyl group, a linear alkyl group having from 1 to 10 carbon atoms, a mono or difluoroalkyl group having from i to 10 carbon atoms, a branched alkyl group having from 3 to 8 carbon atoms, an alkoxyalkyl group having from 2 to 7 carbon atoms or an alkenyl group having from 2 to 8 carbon atom. This compound is readily prepared from a silacyclohexanone compound of the following formula (XV) which we proposed in Japanese Patent Application No. No. 6-71825, filed Mar. 24, 1994.

wherein Ar and R have, respectively, the same meanings as defined with respect to the formula (I).

For instance, according to the following reaction sequence (XVI), a ylide compound obtained from an alkoxymethyltriphenylphosphonium salt by the action of a base and the silacyclohexane compound are subjected to the Wittig reaction to obtain an alkyl enol ether, followed by hydrolysis with an add catalyst to obtain the silacyclohexane carbaldehyde of the formula (I)

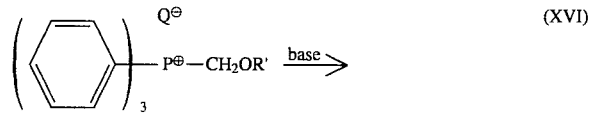

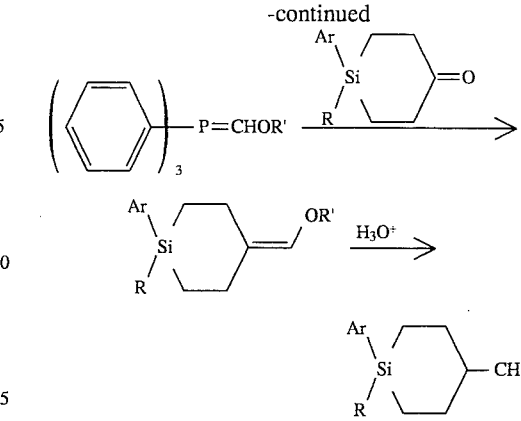

wherein R' represents an alkyl group having from 1 to 10 carbon atoms, preferably from 1 to 4 carbon atoms and Q represents a halogen preferably including Cl, Br or I.

Examples of the alkoxymethyltriphenylphosphonium salt include methoxymethyltriphenylphosphonium chloride, methoxymethyltriphenylphosphonium bromide, methoxymethyltriphenylphosphonium iodide, ethoxymethyltriphenylphosphonium chloride, ethoxymethyltriphenylphosphonium bromide, ethoxymethyltriphenylphosphonium iodide and the like.

The bases used for the formation of the ylide compound include organolithium compounds such as n-butyl lithium, s-butyl lithium, t-butyl lithium, methyl lithium, phenyl lithium and the like, alkoxides such as sodium methoxide, sodium ethoxide, potassium t-butoxide and the like, and dimsyl sodium.

The reaction is effected in solvents including ethers such as tetrahydrofuran, diethyl ether, di-n-butyl ether, 1,4-dioxane and the like or mixed solvents of the ethers with hydrocarbons such as n-hexane, n-heptane, iso-octane, benzene, toluene, xylene, cumene and the like or aprotic polar solvents such as N,N-dimethylformamide, dimethylsulfoxide, hexamethylphosphoric triamide and the like.

The silacyclohexane compound is then added to the resultant ylide compound formed in the solvent to cause the Wittig reaction to proceed thereby obtaining an alkyl ether compound.

The alkyl ether compound is hydrolyzed in the presence of an acid catalyst. Examples of the acid include inorganic acids such as hydrochloric acid, sulfuric acid and the like, and organic acids such as oxalic acid, trifluoroacetic acid, chloroacetic acid and the like.

The reactions in the sequence (XVI) and the hydrolysis of the alkyl ether compound proceed under relatively wide reaction conditions including a preferred range of temperature of from 0° to 80° C., more preferably from 10° to 40° C. In view of economy, these reactions are optimally carried out at normal temperatures without resorting to any specific techniques and apparatus.

The reaction time may be appropriately controlled in these steps while taking the types of groups being reacted with each other and the reaction may be continued until the reactions in the respective steps are completed.

The thus obtained silacyclohexane carbaldehyde compounds may be used for the preparation of various types of silacyclohexane-based liquid crystal compounds. The processes for preparing derivatives of the silacyclohexane carbaldehyde compounds are then described.

It should be noted that the preparation of the liquid crystal compounds may be performed under relatively wide temperature and time conditions as in the case of the preparation of the carbaldehyde compounds and that the reaction conditions as will be set out in the respective steps are not for limitation. Most steps favorably proceed at normal temperatures and normal pressures although higher temperatures and/or higher pressures may be used if a higher reaction velocity is required. In this sense, the reaction conditions including the reaction temperature substantially in all the steps are not critical.

First, when phosphorus ylide compounds which are readily prepared from a corresponding phosphonium salt by the action of bases are reacted with the silacyclohexane carbaldehyde compounds according to the following reaction sequence (XVII), olefinic compounds are obtained through the Wittig reaction The silacyclohexane carbaldehyde compound is then added to the thus obtained ylide compounds formed in the solvents, whereupon the Wittig reaction is caused to proceed to obtain an olefinic compound.

The thus obtained olefinic compound is subjected to catalytic reduction thereby hydrogenating the double bond thereof to obtain a saturated compound.

This catalytic reduction proceeds according to the following reaction formula (XVIII)

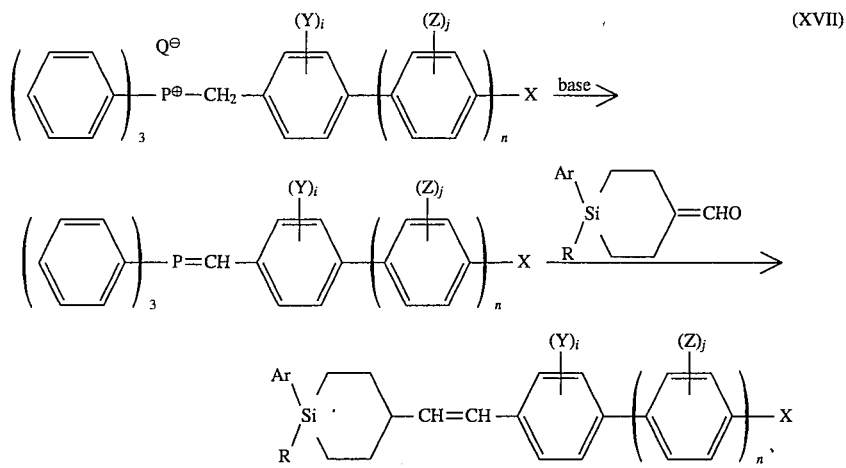

(XVII)

wherein Q, Y, Z, X, Ar, R, i and j have, respectively, the same meanings as defined hereinbefore and n is a value of 0 or 1.

The bases useful for the formation of ylides include organolithium compounds such as n-butyl lithium, s-butyl lithium, t-butyl lithium, methyl lithium, phenyl lithium and the like, alkoxides such as sodium methoxide, sodium ethoxide, potassium t-butoxide and the like, and dimsyl sodium.

The reactions are effected in solvents including ethers such as tetrahydrofuran, diethyl ether, di-n-butyl ether, 1,4-dioxane and the like, or mixtures of the ethers with aprotic polar solvents including hydrocarbons such as n-hexane, n-heptane, iso-octane, benzene, toluene, xylene, cumene and the like, N,N-dimethylformamide, dimethylsulfoxide, hexamethylphosphoric triamide and the like. These reactions are effected preferably at a temperature of from 0° to 80° C., more preferably from 10° to 40° C. for a time sufficient to complete the reaction.

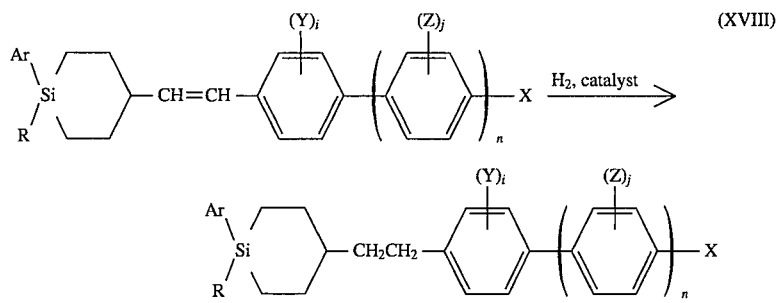

(XVIII)

The catalysts used for the hydrogenation include, for example, metals such as palladium, platinum, rhodium, nickel, ruthenium and the like. Better results are obtained when using palladium-carbon, palladium-barium sulfate, palladium-diatomaceous earth, platinum oxide, platinum-carbon, rhodium-carbon, Raney nickel and the like.

The hydrogenation reaction is carried out by a usual manner. Preferably, the hydrogenation is effected at a temperature ranging from 0° to 150° C., more preferably from 20° to 100° C. A higher pressure of hydrogen results in a higher reaction velocity. In view of limitation on the type of reactor, it is preferred to use a hydrogen pressure of from 5 to 20 kg/cm².

Thereafter, the saturated compound is subjected to desilylation reaction with an electrophilic reagent to obtained a halosilacyclohexane compound, followed by reduction reaction as shown in the following reaction sequence (XIX)

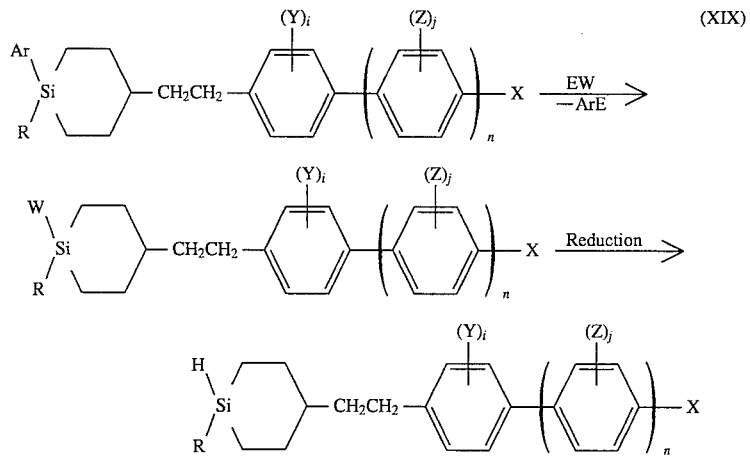

(XIX)

wherein EW is an electrophilic reagent wherein W represents a halogen.

The electrophilic reagents include a halogen, a hydrogen halide, a metal halide, a sulfonic derivative, an add halide, an alkyl halide and the like. Preferably, there are mentioned bromine, iodine, chlorine, iodine monochloride, hydrogen chloride, hydrogen bromide, hydrogen iodide, mercury (II) chloride, trimethylsilyl chlorosulfonate, acetyl chloride, acetyl bromide, benzoyl chloride, t-butyl chloride and the like. In order to increase the reaction velocity, Lewis acids such as aluminium chloride, zinc chloride, titanium tetrachloride, boron trifluoride and the like may be added to the reaction system. Alternatively, the reaction system may be irradiated with actinic light such as ultraviolet rays and/or visible rays.

Preferably, the reaction using the electrophilic agent is carried out at a temperature of from 0° to 80° C., more preferably from 10° to 40° C.

The reagents used for the reduction of the halosilacyclohexane compound include metal hydrides such as sodium hydride, calcium hydride, trialkylsilanes, boranes, dialkyl aluminium compounds and the like, complex hydrides such as sodium borohydride, potassium borohydride, tri-isobutylammonium borohydride and the like, and substituted hydrides thereof such as lithium trialkoxyaluminium hydride, sodium di(methoxyethoxy)aluminium hydride, lithium triethylborohydride, sodium cyanoborohydride and the like.

Although not limitative, the reduction of the halosilacyclohexane is carried out preferably at a temperature of from 0° to 100° C., more preferably from 20° to 70° C.

By the above process, a silacyclohexane-based liquid crystal compound can be prepared.

Among the saturated compounds obtained by the hydrogenation in the reaction formula (XVIII) where n=0, a compound of the following formula (XX)

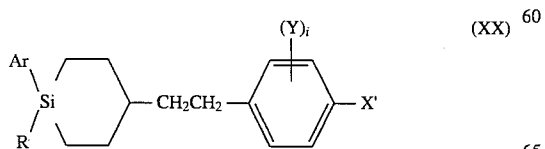

(XX)

wherein Ar, R, Y and i have, respectively, the same meanings as defined hereinbefore and X' represents a halogen preferably including Cl, Br or I, is used to prepare a compound of the following general formula (XXI) which corresponds to the final compound of the general formula (XVIII) wherein n=1

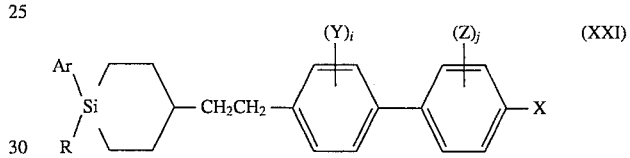

(XXI)

The above reaction proceeds according to the following reaction formula (XXII)

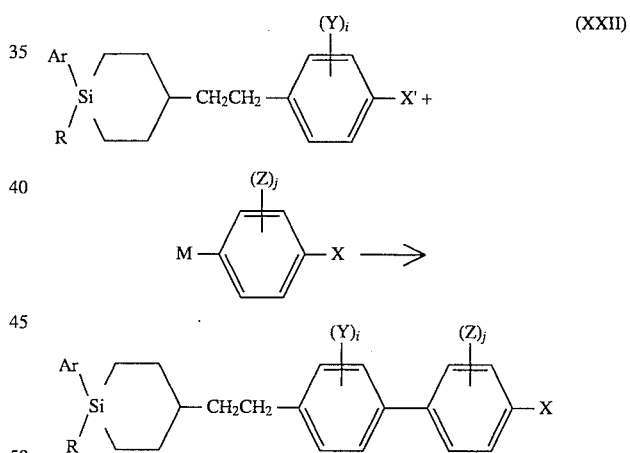

(XXII)

wherein M represents MgU or ZnU wherein U represents a halogen preferably including Cl, Br or I, or $B(OV)_2$ wherein V represents a hydrogen atom or an alkyl group having from 1 to 4 carbon atoms.

This reaction is effected in the presence of a catalyst of a transition metal compound. Preferred examples of the catalyst include palladium or nickel compounds. The palladium catalysts include, for example, zero valent palladium compounds such as tetrakis(triphenylphosphine)palladium (0), di-[1,2-bis(diphenylphosphino)ethane]palladium (0) and the like, compounds consisting of divalent palladium compounds, such as palladium acetate, palladium chloride and the like, and ligands such as triphenylphosphine, 1,2-bis-(diphenylphosphino)ethane and the like, and combinations of those compounds mentioned above with reducing agents.

Examples of the nickel catalyst include divalent nickel compounds such as 1,3-bis (diphenylphosphino)propane nickel (II) chloride, 1,2-bis(diphenylphosphino)ethane nickel (II) chloride, bis(triphenylphosphine) nickel (II) chloride and the like, zero valent nickel compounds such as tetrakis(triphenylphosphine) nickel (0) and the like.

If the organometallic compound used is a boric acid derivative wherein M represents $B(OV)_2$, it is preferred that the reaction is carried out in the presence of a base. In this case, examples of the base include inorganic bases such as sodium carbonate, sodium hydrogencarbonate, potassium carbonate, sodium hydroxide, potassium hydroxide and the like, and organic bases such as triethylamine, tributylamine, dimethylaniline and the like.

The compound obtained according to the reaction formula (XXI) can be converted into a silacyclohexane-based liquid crystal compound according to the reaction sequence (XIX) indicated before.

The thus prepared compounds may be purified by a usual manner such as recrystallization, chromatography or the like, thereby obtaining silacyclohexane-based liquid crystal compounds in an intended trans form, if necessary.

The present invention is more particularly described by way of examples.

EXAMPLE 1

Preparation of
4-n-pentyl-4-phenyl-4-silacyclohexane carbaldehyde 58 g of potassium t-butoxide was added to a mixture of 180 g of methoxymethyltriphenylphosphonium chloride and 200 ml of tetrahydrofuran to prepare an orange ylide solution. 130 g of 4-n-pentyl-4-phenyl-4-silacyclohexanone was dropped in the solution. After agitation at room temperature for 2 hours, the solution was poured into iced water, followed by extraction with ethyl acetate and then by ordinary washing and concentrating operations to obtain a residue. n-Hexane was added to the residue and the resultant crystals of triphenylphosphine oxide were removed by filtration. The resultant filtrate was concentrated to obtain 145 g (quantitative yield) of a crude product of a corresponding methyl enol ether.

The product had the following IR absorption spectra and NMR absorptions.

IR (liquid film)$v_{max}$: 2920, 2840, 1675, 1455, 1235, 1205, 1145, 1110, 855, 695 $cm^{-1}$ $^1$H-NMR (100 MHz, $CDCl_3$): δ 0.60–1.60 (15H, m) 2.06–2.75 (4H, m) 3.53 (3H, s) 5.78 (1H, s) 7.20–7.62 (5H, m) ppm 200 ml of methylene chloride and 200 ml of 20% hydrochloric acid were added to the thus obtained crude product, followed by agitation at room temperature for 5 hours. The methylene chloride phase was collected by separation and subjected to ordinary washing and concentrating operations, followed by purification through silica gel column chromatography to obtain 132 g of the intended product at a yield of 96%.

IR (liquid film)$v_{max}$: 2920, 2860, 1720, 1455, 1425, 1195, 1110, 830, 730, 695 $cm^{-1}$ $^1$H-NMR (100 MHz, $CDCl_3$): δ 1.60–2.40 (20H, m) 7.20–7.75 (5H, m) 9.55, 9.68 (1H, s×2 (two singlets corresponding to two steric isomers being combined to provide a signal corresponding to 1H)) ppm

EXAMPLE 2

The general procedure of Example i was repeated using 4-n-propyl-4-phenyl- 4-silacyclohexanone, thereby obtaining 4-n-propyl-4-phenyl-4-silacyclohexane carbaldehyde with the following results of IR and $^1$H-NMR analyses.

IR (liquid film)$v_{max}$: 2920, 2860, 1720, 1455, 1420, 1195, 1105, 1060, 995, 830, 730, 695 $cm^{-1}$ $^1$H-NMR (100 MHz, $CDCl_3$): δ 0.55–1.95 (13H, m) 2.00–2.40 (3H, m) 7.20–7.70 (5H, m) 9.55, 9.68 (1H, s×2) ppm

EXAMPLE 3

The general procedure of Example 1 was repeated using 4,4'-diphenyl-4-silacyclohexanone, thereby obtaining 4,4-diphenyl-4-silacyclohexane carbaldehyde with the following results of IR and $^1$H-NMR analyses.

IR (liquid film)$v_{max}$: 3060, 2920, 2860, 1720, 1425, 1110, 990, 830, 725, 695 $cm^{-1}$ $^1$H-NMR (100 MHz, $CDCl_3$): δ 0.90–1.92 (6H, m) 1.95–2.45 (3H, m) 7.20–7.75 (10H, m) 9.62 (1H, s) ppm

EXAMPLE 4

The general procedure of Example i was repeated using 4-n-pentyl-4-p-tolyl- 4-silacyclohexanone, thereby obtaining 4-n-pentyl-4-p-tolyl-4-silacyclohexane carbaldehyde with the following results of IR and $^1$H-NMR analyses.

IR (liquid film)$v_{max}$: 2920, 2860, 1725, 1455, 1410, 1195, 1110, 835, 800, 745 $cm^{-1}$ $^1$H-NMR (100 MHz, $CDCl_3$): δ 0.50–2.00 (17H, m) 2.02–2.45 (3H, m) 2.34 (3H, s) 7.10–7.60 (4H, m) 9.55, 9.68 (1H, s×2) ppm

EXAMPLE 5

The general procedure of Example I was repeated using 4-n-propyl-4-p-tolyl- 4-silacyclohexanone, thereby obtaining 4-n-propyl-4-p-tolyl-4-silacyclohexane carbaldehyde with the following results of IR and $^1$H-NMR analyses.

IR (liquid film)$v_{max}$: 2920, 2860, 1720, 1455, 1410, 1200, 1105, 1060, 1000, 795, 740 $cm^{-1}$ $^1$H-NMR (100 MHz, $CDCl_3$): δ 0.50–1.96 (13H, m) 2.00–2.40 (3H, m) 2.34 (3H, s) 7.10–7.60 (4H, m) 9.55, 9.68 (1H, s×2) ppm

EXAMPLE 6

The general procedure of Example i was repeated using 4-ethyl-4-p-tolyl-4 -silacyclohexanone, thereby obtaining 4-ethyl-4-p-tolyl-4-silacyclohexane carbaldehyde with the following results of $^1$H-NMR analysis.

$^1$H-NMR (100 MHz, $CDCl_3$): δ 0.50–1.96 (11H, m) 2.00–2.40 (3H, m) 2.34 (3H, s) 7.10–7.60 (4H, m) 9.55, 9.68 (1H, s×2) ppm

EXAMPLE 7

Preparation of
trans-4-(2-(4-ethoxyphenyl)ethyl)-1-n-pentyl-1-silacyclohexane 65 ml of an n-hexane solution of 1.60 moles of n-butyl lithium was added to a mixture of 48.0 g of p-ethoxybenzyltriphenylphosphonium bromide and 200 ml of tetrahydrofuran to obtain a ylide solution. 27.4 g of 4-n-pentyl-4-phenyl-4 -silacyclohexane carbaldehyde was dropped in the solution. After agitation at room temperature for 2 hours, the resultant solution was charged into iced water and extracted with ethyl acetate. The extract was subjected to ordinary washing and concentrating operations to obtain a residue, to which n-hexane was added. The resultant crystals of triphenylphosphine oxide were removed by filtration and the flitrate was concentrated. The resultant residue was purified through silica gel column chromatography to obtain 38.0 g (yield: 97%) of 4-(2-(4-ethoxyphenyl)ethenyl)-1-n-pentyl-1-phenyl-1-silacyclohexane.

The results of IR and $^1$H-NMR analyses are as follows. IR (liquid film)$v_{max}$: 2920, 1605, 1510, 1240, 1170, 1100, 1045, 960, 795, 695 cm$^{-1}$ $^1$H-NMR (100 MHz, CDCl$_3$): δ 0.56–2.30 (23H, m) 4.00, 4.02 (2H, qx2) 5.80–6.44 (2H, m) 6.60–7.64 (9H, m) ppm 36.0 g of the thus obtained 4-(2-(4-ethoxyphenyl)ethenyl)-1-n-pentyl-1-phenyl-1-silacyclohexane was dissolved in 100 ml of ethyl acetate, followed by hydrogenation at a pressure of 5 kg/cm$^2$ of hydrogen at room temperature in the presence of 200 mg of palladium-carbon used as a catalyst. After the hydrogen had been consumed theoretically, the catalyst was removed by filtration and the resultant flitrate was concentrated to obtain 36.2 g (quantitative yield) of 4-(2-(4-ethoxyphenyl)ethyl)-1-n-pentyl-1-phenyl-1-silacyclohexane.

IR (liquid film)$v_{max}$: 2920, 2860, 1610, 1510, 1240, 1175, 1110, 1045, 815, 695 cm$^{-1}$ $^1$H-NMR (100 MHz, CDCl$_3$): δ 0.56–1.70 (20H, m) 1.48 (3H, t) 1.70–2.16 (2H, m) 2.40–2.70 (2H, m) 3.97 (2H, q) 6.70–6.90 (2H, m) 6.90–7.20 (2H, m) 7.22–7.62 (5H, m) ppm 100 ml of a carbon tetrachloride solution of 1.0 mole of iodine monochloride was added to 35.0 g of the thus obtained 4-(2-(4-ethoxyphenyl)ethyl)-1-n-pentyl-1-phenyl-1-silacyclohexane at room temperature, followed by agitation at room temperature for 1 hour and then concentration. The resultant residue was dissolved in 100 ml of tetrahydrofuran and dropped in 100 ml of a mixture of 10.0 g of lithium aluminium hydride and 100 ml of tetrahydrofuran at 0° C. The reaction mixture was agitated at room temperature for 1 hour, after which it was poured into 200 ml of a 5% hydrochloric acid solution, followed by extraction with ethyl acetate. After ordinary washing, drying and concentrating operations, the resultant concentrate was purified through silica gel column chromatography to obtain 19.2 g of the intended product (yield: 68%).

IR (liquid film)$v_{max}$: 2918, 2852, 2098, 1612, 1512, 1244, 1051, 887, 821 cm$^{-1}$ $^1$H-NMR (270 MHz, CDCl$_3$): δ 0.54–0.84 (4H, m) 0.96–1.15 (5H, m) 1.24–1.72 (14H, m) 2.10–2.25 (2H, m) 2.63–2.73 (2H, t) 3.88–4.00 (1H, m) 4.08 (2H,q) 6.85–7.00 (2H, m) 7.10–7.25 (2H, m) ppm

EXAMPLE 8

The general procedure of Example 7 was repeated using 4-n-pentyl-4-phenyl- 4-silacyclohexane carbaldehyde and a ylide compound obtained from p-fluorobenzyltriphenylphosphonium bromide, thereby obtaining trans-4-(2-(4-fluorophenyl)ethyl)-1-n-pentyl-1-silacyclohexane with the following results of IR and $^{13}$C-NMR analyses.

IR (liquid film)$v_{max}$: 2918, 2852, 2098, 1601, 1510, 1223, 887, 823 cm$^{-1}$ $^{13}$C-NMR (67.5 MHz, CDCl$_3$): 9.52 (s), 12.06 (s), 13.99 (s), 22.37 (s), 24.11 (s), 31.44 (s), 32.73 (s), 35.40 (s), 39.39 (s), 39.85 (s), 114.92 (d), 129.55 (d), 138.61 (d), 161.12 (d)ppm

EXAMPLE 9

The general procedure of Example 7 was repeated using 4-n-pentyl-4-phenyl- 4-silacyclohexane carbaldehyde and a ylide compound obtained from 3,4-difluorobenzyltriphenylphosphonium bromide, thereby obtaining trans-4-( 2-(3, 4-difluorophenyl)ethyl)-1-n-pentyl-1-silacyclohexane with the following results of IR and $^1$H-NMR analyses.

IR (liquid film)$v_{max}$: 2920, 2852, 2100, 1608, 1520, 1284, 1211, 887, 818 cm$^{-1}$ $^1$H-NMR (270 MHz, CDCl$_3$): δ 0.38–0.64 (4H, m) 0.80–0.95 (5H, m) 1.10–1.56 (11H, m) 1.94–2.04 (2H, m) 2.50–2.60 (2H, m) 3.66–3.78 (1H, m) 6.84–7.10 (3H, m) ppm

EXAMPLE 10

The general procedure of Example 7 was repeated using 3-methylbutyl-4-phenyl-1-silacyclohexane carbaldehyde and a ylide compound obtained from p-fluorobenzyltriphenylphosphonium bromide, thereby obtaining trans-4-(2-(4-fluorophenyl)ethyl)-1-(3-methylbutyl)-1-silacyclohexane with the following results of IR and $^1$H-NMR analyses and a C-I transition temperature.

IR (liquid film)$v_{max}$: 2916, 2848, 2098, 1510, 1223, 889, 823 cm$^{-1}$

C-I transition temperature: −10.5° C.

$^1$H-NMR (270 MHz, CDCl$_3$): δ 0.50–0.62 (4H, m) 0.88–0.95 (8H, m) 1.20–1.28 (5H, m) 1.47–1.52 (3H, m) 2.00–2.02 (2H, m) 2.57–2.61 (2H, m) 3.70–3.80 (1H, m) 6.94–6.98 (2H, m) 7.10–7.14 (2H, m) ppm

EXAMPLE 11

The general procedure of Example 7 was repeated using (3-methoxypropyl)-4-phenyl-1-silacyclohexane carbaldehyde and a ylide compound obtained from p-fluorobenzyltriphenylphosphonium bromide, thereby obtaining trans-4-(2-(4-fluorophenyl)ethyl)-1-(3-methoxypropyl)-1 -silacyclohexane with the following results of IR and $^1$H-NMR analyses and a C-I transition temperature.

IR (liquid film)$v_{max}$: 2920, 2852, 2098, 1510, 1223, 1221, 1119, 887, 823 cm$^{-1}$ C-I transition temperature: −6.7° C.

$^1$H-NMR (270 MHz, CDCl$_3$): δ 0.42–0.52 (4H, m) 0.57–0.64 (8H, m) 0.88–0.94 (2H, m) 1.17–1.30 (3H, m) 1.42–1.50 (2H, m) 1.55–1.66 (2H, m) 1.97–2.01 (2H, m) 2.53–2.59 (2H, m) 3.30–3.35 (5H, m) 3.72–3.76 (1H, m) 6.90–6.96 (2H, m) 7.07–7.24 (2H, m) ppm

EXAMPLE 12

The general procedure of Example 7 was repeated using 4-pentenyl-4-phenyl-1-silacyclohexane carbaldehyde and a ylide compound obtained from p-fluorobenzyltriphenylphosphonium bromide, thereby obtaining trans-4-(2-(4 -fluorophenyl)ethyl)-1-(4-pentenyl)-1-silacyclohexane with the following results of IR and $^1$H-NMR analyses and a C-I transition temperature.

IR (liquid film)$v_{max}$: 2918, 2852, 2098, 1510, 1223, 1115, 887, 823 cm$^{-1}$ C-I transition temperature: −23.9° C.

$^1$H-NMR (270 MHz, CDCl$_3$): δ 0.49–0.51 (2H, m) 0.59–0.66 (2H, m) 0.90–0.95 (2H, m) 1.21–1.28 (3H, m) 1.40–1.52 (4H, m) 1.99–2.12 (4H, m) 2.55–2.61 (2H, m) 3.72–3.77 (1H, m) 4.95–5.04 (2H, m) 5.72–5.87 (1H, m) 6.92–6.98 (2H, m) 7.08–7.14 (2H, m) ppm

EXAMPLE 13

The general procedure of Example 7 was repeated using n-pentyl-4-phenyl- 1-silacyclohexane carbaldehyde and a ylide compound obtained from 2,3-difluoro-4-ethoxybenzyltriphenylphosphonium bromide, thereby obtaining trans-4-(2-(2,3-difluoro-4-ethoxyphenyl)ethyl)-1-(n-pentyl)-1-silacyclohexane with the following results of IR and $^1$H-NMR analyses and C-I and N-I transition temperatures.

IR (liquid film)$v_{max}$: 2956, 2920, 2852, 2098, 1639, 1512, 1479, 1292, 1080, 887, 831, 816 cm$^{-1}$ C-I transition temperature: 12.4° C.

N-I transition temperature: −17.8° C.

$^1$H-NMR (270 MHz, CDCl$_3$): δ 0.41–0.63 (3H, m) 0.86–0.95 (5H, m) 1.19–1.50 (14H, m) 2.00–2.04 (2H, m) 2.55–2.61 (2H, m) 3.73–3.77 (1H, m) 4.03–4.10 (2H, m) 6.59–6.66 (1H, m) 6.75–6.82 (1H, m) ppm

EXAMPLE 14

Preparation of 4-(2-(trans-4-n-propyl-4-silacyclohexyl)ethyl)-3',4'-difluorophenyl In the same manner as in Example 7, 26.0 g of 4-n-propyl-4-p-tolyl-4-silacyclohexane carbaldehyde and 50.0 g of a ylide compound obtained from 4-(3,4-difluorophenyl)benzyltriphenylphosphonium bromide and potassium t-butoxide were interacted to obtain an olefinic compound according to the Wittig reaction,, followed by hydrogenation reaction in the presence of a palladium-carbon catalyst to obtain 37.6 g (yield: 84%) of 4-(2-(4-n-propyl-4-p-tolyl-4-silacyclohexyl)ethyl)-3',4'-difluorobiphenyl.

IR (liquid film)$v_{max}$: 2920, 1600, 1525, 1500, 1305, 1260, 1100, 805, 765 cm$^{-1}$ $^1$H-NMR (100 MHz, CDCl$_3$): δ 0.55–1.75 (16H, m) 1.76–2.20 (2H, m) 2.36 (3H, s) 2.46–2.80 (2H, m) 7.00–7.54 (11H, m) ppm The thus obtained 4-(2-(4-n-propyl-4-p-tolyl-4-silacyclohexyl)ethyl)-3',4'-difluorobiphenyl was subjected to de-silylation reaction with iodine monochloride in the same manner as in Example 7, followed by reduction reaction with lithium aluminium hydride to obtain 19.3 g of the intended product (yield: 69%).

IR (liquid film)$v_{max}$: 2924, 2852, 2087, 1603, 1506, 1308, 1279, 814 cm$^{-1}$ $^1$H-NMR (270 MHz, CDCl$_3$): δ 0.46–0.70 (4H, m) 0.92–1.05 (5H, m) 1.24–1.36 (3H, m) 1.36–1.50 (2H, m) 1.52–1.64 (2H, m) 2.04–2.16 (2H, m) 2.64–2.73 (2H, m) 3.76–3.87 (1H, m) 7.13–7.49 (7H, m) ppm

EXAMPLE 15

Preparation of 4-(2-(trans-4-n-pentyl-4-silacyclohexyl)ethyl)3',4'-difluorobiphenyl In the same manner as in Example 7, 54.9 g of 4-n-pentyl-4-phenyl-4-silacyclohexane carbaldehyde and 52.0 g of a ylide compound obtained from 4-bromobenzyltriphenylphosphonium bromide and potassium t-butoxide to obtain 75.2 g (yield: 88%) 4-(2-(4-bromophenyl)ethenyl)-1-n-pentyl-1-phenyl-1-silacyclohexane which was made of a mixture of cis-trans isomers relative to the silacyclohexane ring and the double bond yielding four peaks when subjected to gas chromatography, both isomers having a GC-MS (gas chromatography-mass spectroscopy, 70 eV) (m/z)$^+$ of 426 (M$^+$).

42.8 g of 4-(2-(4-bromophenyl)ethenyl)-1-n-pentyl-1-phenyl-1-silacyclohexane was dissolved in 200 ml of ethanol at room temperature and then hydrogenated at normal pressures in the presence of a catalyst made of 200 mg of platinum oxide. After consumption of a theoretical amount of hydrogen, the catalyst was removed by filtration and the resultant flitrate was concentrated. 200 ml of tetrahydrofuran and 180 mg of tetrakis(triphenylphosphine) palladium (0) were added to the resulting residue. Thereafter, 120 ml of a tetrahydrofuran solution of 1.0 mole of 3,4-difluorophenylzinc chloride, followed by agitation at 40° C. for 12 hours. The reaction mixture was poured into an ammonium chloride aqueous solution and extracted with ethyl acetate. After ordinary washing, drying and concentrating operations, the resultant product was purified through silica gel column chromatography to obtain 39.6 g (yield: 86%) of 4-(2-(4-n-pentyl-4-phenyl-4-silacyclohexyl)ethyl-3',4'-difluorobiphenyl.

IR (liquid film)$v_{max}$: 2920, 1600, 1525, 1500, 1310, 1260, 1110, 1100, 805, 765 cm$^{-1}$ $^1$H-NMR (100 MHz, CDCl$_3$): δ 0.55–1.72 (20H, m) 1.76–2.22 (2H, m) 2.46–2.80 (2H, m) 7.00–7.60 (12H, m) ppm In the same manner as in Example 7, 39.0 g of the thus obtained 4-(2-(4-n-pentyl-4-phenyl-4-silacyclohexyl)ethyl-3',4'-difluorobiphenyl was subjected to de-silylation reaction with iodine monochloride and then to reduction reaction with lithium aluminium hydride to obtain 17.9 g of the intended product (yield: 55%).

IR (liquid film)$v_{max}$: 2920, 2850, 2100, 1605, 1504, 1311, 1267, 814 cm$^{-1}$ $^1$H-NMR (270 MHz, CDCl$_3$): δ 0.40–0.65 (4H, m) 0.82–0.97 (5H, m) 1.15–1.46 (9H, m) 1.48–1.60 (2H, m) 1.98–2.08 (2H, m) 2.60–2.68 (2H, m) 3.68–3.78 (1H, m) 7.15–7.49 (7H, m) ppm As will be apparent from the foregoing description, the silacyclohexane carbaldehyde compound of the invention is a useful intermediate for preparing liquid crystal compounds and can thus be used to derive various types of silacyclohexane-based liquid crystal compounds therefrom. For the preparation of the derivatives, the reactions in the respective steps substantially proceed at normal temperatures under normal pressures for several tens minutes to ten and several hours as will become apparent from the examples although higher or lower temperatures and/or pressures may be used, if desired.

What is claimed is:

1. A silacyclohexane carbaldehyde compound of the following formula (I)

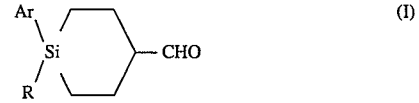

wherein Ar represents a phenyl group or a tolyl group, and the R is selected from the group consisting of a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms and an alkenyl group having from 2 to 8 carbon atoms.

2. A process for preparing a silacyclohexane-based liquid crystal compound which comprises:

reacting a silacyclohexane carbaldehyde of the following general formula

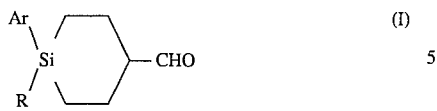

wherein Ar represents a phenyl group or a tolyl group, and the R is selected from the group consisting of a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms and an alkenyl group having from 2 to 8 carbon atoms, with a ylide compound of the following general formula

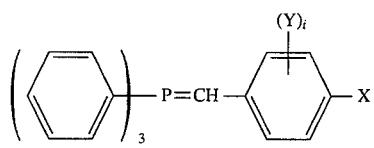

wherein the X is selected from the group consisting of CN, F, Cl, $CF_3$, $CClF_2$, $CHClF$, $OCF_3$, $OCClF_2$, $OCHF_2$, $OCHClF$, $(O)_mCT=CX_1X_2$, $O(CH_2)_r(CF_2)_sX_3$, R and OR wherein $m$ is a value of 0 or 1, T and $X_1$ independently represent H, F or Cl, $X_2$ represents F or Cl, r and s are, respectively, a value of 0, 1 or 2 provided that r+ s= 2, 3 or 4, and $X_3$ represents H, F or Cl, and R has the same meaning as defined above, Y represents a halogen or a methyl group, i is a value of 0, 1 or 2, thereby obtaining a compound of the following formula

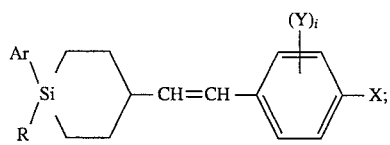

subjecting the thus obtained compound to hydrogenation to obtain a compound of the following general formula

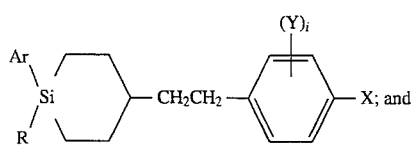

further subjecting the thus obtained compound to desilylation and then to reduction to obtain a silacyclohexane-based liquid crystal compound of the

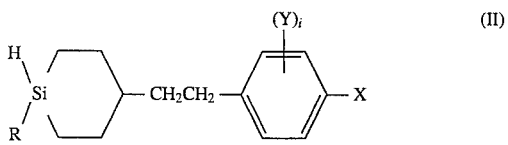

3. A process according to claim 2, wherein said desilylation is caused by an electrophilic reagent.

4. A process according to claim 3, wherein said desilylation is caused after addition of a Lewis acid or under irradiation of light.

5. A process according to claim 2, wherein the reduction is caused by addition of a member selected from the group consisting of metal hydrides, complex hydrides and substituted hydrides thereof.

6. A process for preparing a silacyclohexane-based liquid crystal compound with comprises:

reacting a silacyclohexane carbaldehyde of the following general formula

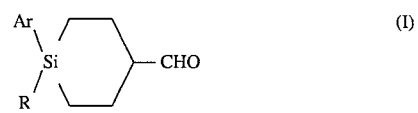

wherein Ar represents a phenyl group or a tolyl group, and the R is selected from the group consisting of a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms and an alkenyl group having from 2 to 8 carbon atoms, with a ylide compound of the following general formula

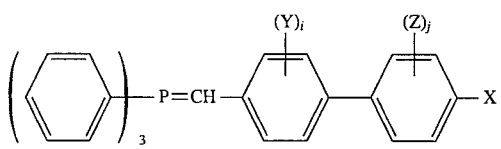

wherein the X is selected from the group consisting of CN, F, Cl, $CF_3$, $CClF_2$, $CHClF$, $OCF_3$, $OCClF_2$, $OCHF_2$, $OCHClF$, $(O)_mCT=CX_1X_2$, $O(CH_2)_r(CF_2)_sX_3$, R and OR wherein j is a value of 0 or 1, T and $X_1$ independently represent H, F or Cl, $X_2$ represents F or Cl, r and s are, respectively, a value of 0, 1 or 2 provided that r+s=2, 3 or 4, $X_3$ represents H, F or Cl, and R has the same meaning as defined before, Y and Z independently represent a halogen or a methyl group, i and j are independently a value of 0, 1 or 2, thereby obtaining a compound of the following general formula

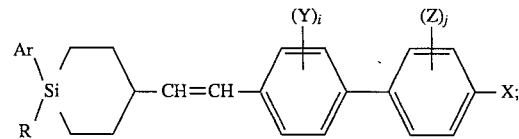

subjecting the compound of the above formula to hydrogenation to obtain a compound of the following general formula

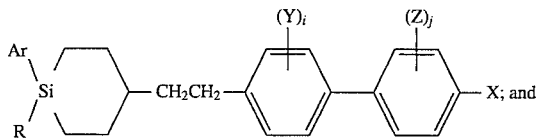

further subjecting the thus obtained compound of the formula to desilylation and then to reduction to obtain a silacyclohexane-based liquid crystal compound of the general formula (III)

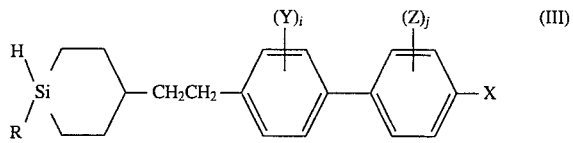

7. A process according to claim 6, wherein said desilylation is caused by an electrophilic reagent.

8. A process according to claim 7, wherein said desilylation is caused after addition of a Lewis acid or under irradiation of light.

9. A process according to claim 6, wherein the reduction is caused by addition of a member selected from the group consisting of metal hydrides, complex hydrides and substituted hydrides thereof.

10. A process for preparing a silacyclohexane-based liquid crystal compound with comprises:

reacting a silacyclohexane carbaldehyde of the following general formula

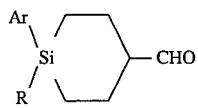 (I)

wherein Ar represents a phenyl group or a tolyl group, and the R is selected from the group consisting of a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms and an alkenyl group having from 2 to 8 carbon atoms, with a ylide compound of the following general formula

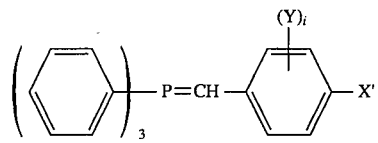

wherein X' represents a halogen, Y represents a halogen or a methyl group, and i is a value of 0, 1 or 2, thereby obtaining a compound of the following general formula

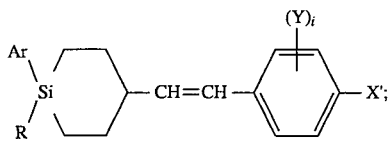

subjecting the compound of the above formula to hydrogenation to obtain a compound of the following general formula

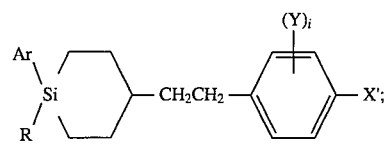

further subjecting the thus obtained compound of the formula to reaction with an organometal compound of the following general formula in the presence of a transition metal catalyst

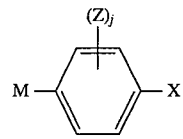

wherein M represents MgU or ZnU wherein U represents a halogen, or B(OV)$_2$ wherein V represents a hydrogen atom or an alkyl group and Z represents a halogen or a methyl group, j is a value of 0, 1 or 2, thereby obtaining a compound of the following general formula

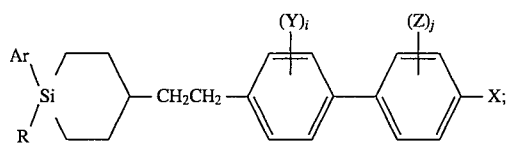

subjecting the compound of the above formula to desilylation and then to reduction to obtain a silacyclohexane-based liquid crystal compound of the following general formula (III)

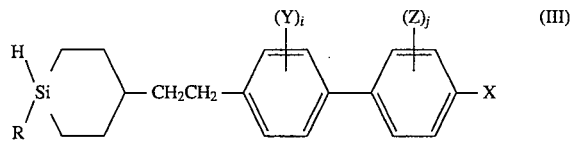

11. A process according to claim 10, wherein said desilylation is caused using an electrophilic reagent.

12. A process according to claim 11, wherein said desilylation is caused after addition of a Lewis acid or under irradiation of light.

13. A process according to claim 10, wherein the reduction is caused by addition of a member selected from the group consisting of metal hydrides, complex hydrides and Substituted hydrides thereof.

14. A process according to claim 10, wherein M representing said organometal compound is B(OV)$_2$ wherein V is H or an alkyl group, whereupon the reaction is under basic conditions.

* * * * *